(12) United States Patent
Pfanner

(10) Patent No.: US 8,059,851 B2
(45) Date of Patent: Nov. 15, 2011

(54) HEARING PROTECTION AND/OR LOUDSPEAKER ELEMENT

(76) Inventor: Anton Pfanner, Hohenems (AT)

( * ) Notice: Subject to any disclaimer, the term of this patent is extended or adjusted under 35 U.S.C. 154(b) by 1289 days.

(21) Appl. No.: 11/573,813

(22) PCT Filed: Aug. 12, 2005

(86) PCT No.: PCT/EP2005/008811
§ 371 (c)(1),
(2), (4) Date: Feb. 16, 2007

(87) PCT Pub. No.: WO2006/018250
PCT Pub. Date: Feb. 23, 2006

(65) Prior Publication Data
US 2007/0269072 A1    Nov. 22, 2007

(30) Foreign Application Priority Data
Aug. 19, 2004   (AT) .................. A 1394/2004

(51) Int. Cl.
*H04R 25/00* (2006.01)

(52) U.S. Cl. ......... 381/379; 381/374; 381/376; 181/130

(58) Field of Classification Search .......... 381/374, 381/376, 379, 383; 181/130
See application file for complete search history.

(56) References Cited

U.S. PATENT DOCUMENTS

| 997,673 | A | | 7/1911 | Hegge | |
|---|---|---|---|---|---|
| 1,225,422 | A | | 5/1917 | Feher | |
| 3,110,356 | A | * | 11/1963 | Mendelson | 181/130 |
| 3,970,082 | A | * | 7/1976 | Leight | 128/866 |
| 4,682,363 | A | * | 7/1987 | Goldfarb et al. | 381/74 |
| 4,972,491 | A | * | 11/1990 | Wilcox, Jr. | 381/375 |
| 5,438,626 | A | * | 8/1995 | Neuman et al. | 381/383 |
| 5,475,449 | A | * | 12/1995 | Pyle | 351/123 |
| 6,382,213 | B1 | * | 5/2002 | Sanpei | 128/864 |
| 6,721,433 | B2 | * | 4/2004 | Sato | 381/379 |
| 7,512,414 | B2 | * | 3/2009 | Jannard et al. | 455/556.1 |
| 2002/0012441 | A1 | * | 1/2002 | Matsunaga et al. | 381/381 |

FOREIGN PATENT DOCUMENTS

| DE | 3722465 | 1/1988 |
|---|---|---|
| DE | 9309795.6 | 11/1993 |
| EP | 0646333 | 9/1994 |
| GB | 623131 | 5/1949 |
| GB | 2336291 | 10/1999 |
| WO | 98/56268 | 12/1998 |

* cited by examiner

*Primary Examiner* — Curtis Kuntz
*Assistant Examiner* — Ryan Robinson
(74) *Attorney, Agent, or Firm* — Volpe and Koenig, P.C.

(57) ABSTRACT

A hearing protection and/or loudspeaker element (1) is provided which includes a carrier part (2) arranged on a protective helmet (5) and a module (4) which can be actively connected to an outer ear of the wearer to act as a hearing protection and/or loudspeaker module. The carrier part (2) and protective helmet can be fixed to the head of the wearer. The module (4) which acts as the hearing protection and/or loudspeaker module can be adjusted in relation to the loudspeaker part (2) and shifted from a position of rest to a position of use. The module (4) itself is like a plug and is embodied as a part that covers the entrance of the human outer ear.

9 Claims, 1 Drawing Sheet

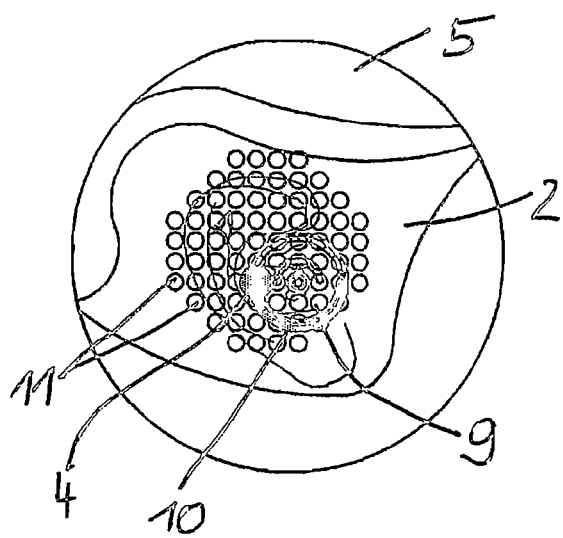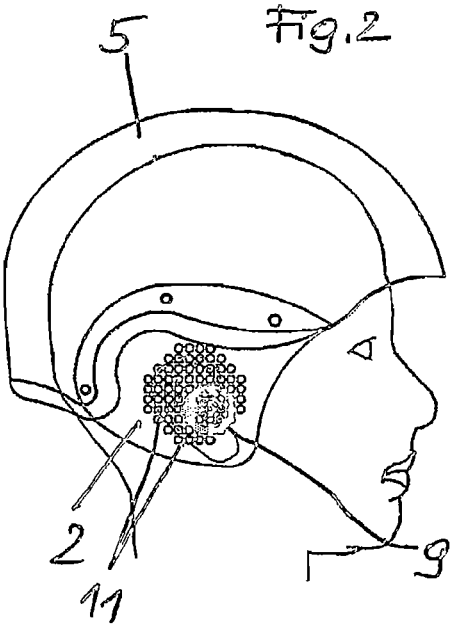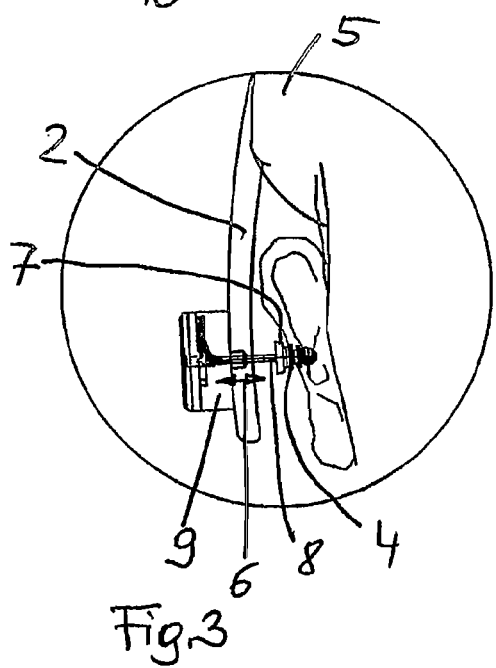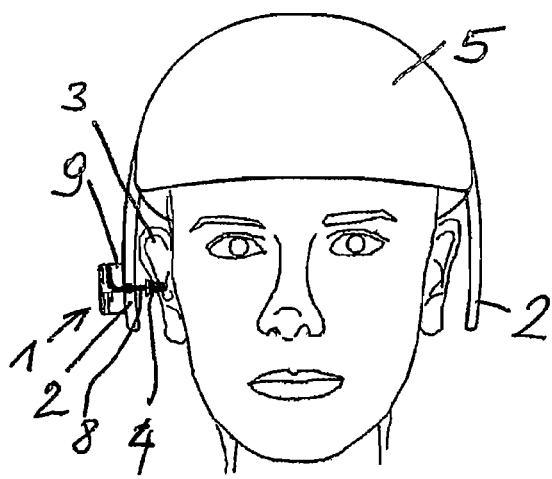

HEARING PROTECTION AND/OR LOUDSPEAKER ELEMENT

BACKGROUND

The invention relates to a hearing protection and/or loudspeaker element with a carrier part and a module that can be effectively connected to an ear of the user acting as a hearing protection and/or a loudspeaker, with the carrier part being fixable to the head of the user.

A multitude of various embodiments of protective helmets and mounting systems for fixing protective hearing cups to a protective helmet have become known. In a known arrangement (EP 0646333 B1) the protective hearing cups are held to the protective helmet pivotally via cantilevers, which must make contact in the position of use, i.e. in the area of the ear of the user, with an appropriate pressure such that the ears are protected from noise occurring. Here, not only a particularly large protective hearing cup is necessary, because the entire ear must be covered, but it is also disadvantageous that the user is subjected to enormous heat, because the pressing protective hearing cups lead to a particularly intense perspiration.

Further, an embodiment of an ear protection is known (U.S. Pat. No. 997,673) in which cups covering the entire ear are arranged on an arc-shaped holding bar guided over the head of the user. Although the cups covering the entire ear as well as the plugs that can be inserted into the ear are held to the holding bar in an adjustable manner, they require prior setting. After positioning this hearing protection, the cups contact the ears and/or cover the area of the ear and the plugs are inserted into the auditory canal. An adjustment or setting of the plugs in reference to the cups is not possible when the hearing protection is worn. Additionally, here the ears of the user always have to be covered in their entirety. Again, the protective hearing measures embodied as cups lead to a particular perspiration when it is hot.

Further, a protective helmet has become known (DE 3722465 A1) in which a pumping device is mounted at the helmet and can be operated at the outside, accessible from the outside of the helmet, in order to inflate two bellows, each of which is arranged between the helmet and an allocated noise-insulating ears cover. The ears covers are mounted to the helmet. The bellows can be deflated by ventilation devices using an operating element accessible from the exterior of the helmet, when the protective helmet is to be taken off. Here, too, ears covers that cover the entire ear of the user and make contact with a respective pressure are provided, which lead to perspiration and thus they are frequently not used for that very reason.

SUMMARY

The invention is therefore based on the object of providing a hearing protection and/or loudspeaker element of the type mentioned at the outset, which is easy to be worn by the user and primarily can be put on and taken off quickly and easily.

According to the invention this is attained in that the module effective as a hearing protection and/or a loudspeaker is adjustable in reference to the carrier part from a position of rest into an position of use and that the module is embodied like a plug and, if necessary as a part covering the entry of the auditory canal of a human ear, and that the module is connected to a carrier part via an elastically stretchable and compressible and/or spring-like embodied holding element.

This measure according to the invention allows the module to be quickly brought into a position of use, is light weight, and primarily covers the entry of the auditory canal only. Thus, no perspiration occurs due to any contacting modules, yet it is still ensured that the auditory canal is effectively protected from an existing noise.

The measure according to the invention ensures that the module, even in case of a potential motion of the carrier part, e.g. together with a helmet, has no rigid effects in reference to the auditory canal and that therefore the occurrence of injuries to the ear can largely be prevented.

The easiest construction results when the module can be deployed from and retracted into the carrier part. In general, only a straight displacement from the carrier part in the direction towards the ear and back, perhaps, is necessary so that the invention also allows various possibilities for a structurally simple design.

In this context it is possible for this module to be connected to the carrier part via a mechanical adjustment device. This is the easiest variant and thus also not very expensive.

More possibilities develop when the module is connected to a carrier part via an electric drive. Then various control elements can be used, in order to improve the possibility for variations even more.

In this context in particular it is therefore possible for the adjustment of the module in reference to the carrier part to occur depending on a predetermined noise level and/or an adjustable loudspeaker. It is therefore possible to set a noise level not yet dangerous for the hearing function. As soon as the noise level is exceeded the module can automatically be deployed into its position of use in the area of the entry to the auditory canal. The same could also be possible when the module is used as a loudspeaker (head phones). As soon as, e.g., a call arrives at the mobile phone, the deployment of the module embodied as a loudspeaker could be initiated. In the same manner the deployment can also be initiated when the user wants to make a call. Here, it is generally possible to integrate a microphone in the loudspeaker and/or headphone, so that environmental noise, such as e.g., the sound of wind, can be excluded when making a telephone call.

Since a hearing protection and/or loudspeaker element according to the invention is provided for the use for respective users, it is provided, of course, that two modules can be arranged offset by 180° in reference to each other on the same carrier part.

An optimum arrangement is provided when the module is adjustable via rotary knobs arranged on the outside of the carrier part. The user then can always deploy the module when the carrier part is put on or even in a helmet worn perhaps or be retracted into the position of rest.

Here, the advantageous design comprises that stops are provided for the deployment range of the module. This excludes damaging the construction itself and the ear of the user as well.

When the module or the adjustment device can be snapped into the deployed position, with the module remaining pivotal in an elastic and/or spring-like fashion, it is ensured that the module cannot be retracted from its deployed protective position unintentionally by normal vibrations. In spite thereof, no injuries can occur, when e.g., the carrier part is forcefully pulled or pushed off the head of the user.

One variant of the exemplary embodiment provides that the holding element is embodied as an elastically bendable rod, inserted into a groove in the rotary knob extending in a circular or spiral-shaped fashion, which is deflected in the deployment area of the module in the deployment direction. Such a rod can e.g., be embodied as a spring element, which is stiff in the axial direction for transferring force, but always allows bending in an elastic spring-like manner. Both in the embodiment as a spring element or as a rod, a type of pipe is formed, by which a cable may also be guided to the module, such as loudspeaker and/or microphone wires.

In order to also allow for the possibility of adjusting to differently sized heads or to various positions of the ears of the user, it is further suggested for the holding element and thus also the module and thus the entire hearing protection and/or loudspeaker element to be held perpendicularly to the deployment direction thereof in a direction adjustable vertically and/or horizontally.

In order to optimally design the hearing protection and /or loudspeaker element according to the invention it is provided that the carrier part is mounted to a helmet, for example a protective helmet, or is a part of such a helmet.

In this way, a carrier part and a module require little material, are light, and can always be used immediately when necessary.

In this context the accessibility of the adjustment means of the hearing protection and/or loudspeaker element is also an essential advantage, of course. Here, it is suggested that the adjustment device for the module can be operated at the exterior surface of the helmet. The adjustment and/or change can be performed by the user himself/herself when the helmet is worn.

The hearing protection and/or loudspeaker element according to the invention may also be provided according to another exemplary embodiment such that two carrier parts are mounted with respective modules to the end regions of an arched part that can be worn. Then, a type of conventional headphones is provided, without requiring cups covering the entire ear of the user being necessary but, for example, support elements only, so that here too only a module embodied in a plug-like fashion is to be adjusted in the direction of the auditory canal. Whether this module is then used as a hearing protection or a loudspeaker or is embodied for both functions is irrelevant.

Another particular use provides that the helmet is embodied as a vehicular protective helmet. Here, hearing protection and/or loudspeaker elements can be provided in the same manner.

BRIEF DESCRIPTION OF THE DRAWINGS

In the following further details of the invention are explained in greater detail using the drawings. Shown are:

FIG. 1 is a frontal view of a head with a protective helmet worn

FIG. 2 is a side view of a head with a protective helmet worn

FIG. 3 is an enlarged detail of a representation according to FIG. 1

FIG. 4 is an enlarged detail of a representation according to FIG. 2

DETAILED DESCRIPTION OF THE PREFERRED EMBODIMENTS

The hearing protection and/or loudspeaker element according to the invention is explained in the following description in connection with a helmet, preferably a protective helmet. Generally other possibilities for using such a hearing protection and/or loudspeaker element may be given, if necessary with an integrated microphone, which are partially discussed in the following description.

The hearing protection and/or loudspeaker element 1 comprises a carrier part 2 and a module 4 effective as a hearing protection and/or loudspeaker, which can be effectively connected to an ear 3 of a user. The carrier part 2 can be fixed to the head of the user. In the example shown, this occurs via a protective helmet 5, on which a carrier part is fixed or perhaps it is connected thereto in one piece. The module 4, effective as a hearing protection and/or loudspeaker 1, is adjustable in reference to the carrier part 2 from a position of rest in the direction of a position of use (arrow direction 6.) The module 4 is embodied like a plug and, if necessary, covers the auditory canal of the human ear 3 with a covering part 7.

The module 4 is connected to the carrier part 2 via an elastically stretchable and/or compressible and/or spring-like holding element 8. Here, the module 4 on the carrier part 2 can be deployed and retracted.

The construction shown in the drawing is the simplest one. Here, the module 4 is connected to the carrier part 2 via a mechanical adjustment device.

Within the scope of the invention, an advantageous embodiment provides to connect the module 4 to the carrier part 2 via an electric drive. Then, a multitude of possibilities can be utilized by measuring devices or various control devices. For example, the adjustment of the module 4 in reference to the carrier part 2 is possible depending on a predetermined noise level and/or an activated loudspeaker. Here, respective control elements can be integrated in the protective helmet 5 or it is possible to cause the module to deploy under control of a measuring device located nearby.

In the representation in FIG. 1, a hearing protection and/or loudspeaker element 1 is arranged only on one side of the protective helmet 5 at the carrier part 2. Of course, the same hearing protection and/or loudspeaker element 1 can also be provided at the opposite side, the right one of the spectator. Also, the two modules 4 are arranged off-set by 180° on the same carrier part 2. It is not necessary for the carrier parts to be identical, when the carrier part or parts 2 are connected to the protective helmet 5.

One construction is particularly advantageous when the module 4 can be adjusted from the exterior by rotary knobs 9 arranged at the carrier part 2. Here, end stops may be provided for the deployment range of the module 4. It is also possible to embody the module 4 or the adjustment device for snapping in the deployed position so that an automatic displacement by vibrations etc. can be avoided. In spite thereof the module 4 remains pivotal in an elastic and/or spring-like manner.

One preferred embodiment provides that the adjustment device for the module 4 can be operated at the exterior surface of the helmet so that an adjustment is possible without having to first take off the helmet or adjust it.

In the construction shown, the holding element 8 is embodied as a rod that can be elastically bent, inserted into a groove 10 extending in a circular or spiral-shaped manner in the rotary knob 9, which is deflected in a deployment direction in a deployment range of the module 4. This rod or an appropriate spring element can be provided with a constant hollow space on the interior, allowing the connecting cable for the headphones and/or an integrated microphone to be fed therethrough.

As particularly discernible from FIGS. 2 and 4, the holding element 8 and thus also the module 4 and thus the entire hearing protection and/or loudspeaker element 1 can be held on the carrier part 2, adjustable in the vertical and/or horizontal direction perpendicularly to the deployment direction thereof. A possibility shown here provides a multitude of holes 11, allowing the possibility for fastening in their area. Here, it is also possible for one or more pins to be provided on the hearing protection and/or loudspeaker element 1, which engage two or more holes 11 at the carrier part so that it allows a torque-proof assembly. This allows an individual adjustment depending on the way the protective helmet 5 is worn by various users and depending on the elevation of the ears or the auditory canal.

In the description it is always assumed that the hearing protection and/or loudspeaker element 1 is seen in connection with a protective helmet 5. The carrier part 2 is then mounted to a helmet, for example a protective helmet, or is a part thereof, perhaps. Additionally, the protective helmet 5 can also be embodied in one piece together with the two carrier parts 2 protruding downwards.

In another embodiment, the two carrier parts 2 with respective modules 4 are mounted to the end regions of an arched part that can be worn. Another possibility provides for the helmet to be embodied as a vehicular protective helmet. Identical or similar conditions also apply and can be attained by the invention when pilot helmets, motorcycle helmets, or other sports helmets are provided.

Within the scope of the invention a multitude of applications are possible for the hearing protection and/or loudspeaker element 1 according to the invention. An application is possible everywhere particular hearing protection is necessary and/or the desire for an immediate loudspeaker is desired. Therefore it is also possible to inform different working teams regarding new locations or measures, which need not occur via heavy and clumsily operated loudspeakers, but an easily displaceable and particularly effective module 4 can be used. In spite thereof, the danger of injuries can be excluded because the module 4 can be pivoted out of the operational position in the auditory canal in an elastic and spring-like fashion.

The structural design of the holding elements 8 and the adjustment device can occur in different fashions. Here, it is always essential and important to allow the deployment of the module 4 in a simple and quick manner and for the module 4, in case of an accident or an unexpected motion of the user and thus a potential displacement of the protective helmet 5 on the head of the user, to be displaced laterally without injuring the ear of the user.

Of course, instead of the relatively small module 4, which can engage the auditory canal, a large cover may also be provided, which can be deployed and retracted in this manner according to the invention, however, here, the essential advantage of the release of the entire ear and thus the prevention of perspiration would be waived.

The invention claimed is:

1. A hearing protection and/or loudspeaker element comprising a carrier part and a module, which can be effectively connected to an ear of a user, acting as a hearing protection and/or a loudspeaker, with the carrier part being adapted to be fastened to a head of the user, the module (4) effective as the hearing protection and/or loudspeaker (1) is adjustable from a position of rest in a direction of a position of use in reference to the carrier part (2) and the module (4) is plug-shaped and is embodied as a part for covering an auditory canal of a human ear, and the module (4) is connected to the carrier part (2) via an elastically stretchable and compressible or spring-type holding element (8) so that the module (4) is elastically and resiliently swingable away from the position of the user in an ear entrance of a user, the module (4) is adjustable by a rotary knob (9) arranged on an outside of the carrier part (2), and the holding element (8) comprises an elastically bendable rod inserted into a circular or spiral-shaped groove (10) of the rotary knob (9).

2. A hearing protection and/or loudspeaker element according to claim 1, wherein the module (4) is held in a deployable and retractable manner to the carrier part (2).

3. A hearing protection and/or loudspeaker element according to claim 1, wherein stops are provided for a displacement area of the module (4).

4. A hearing protection and/or loudspeaker element according to claim 3, wherein the module (4) or an adjustment device for the module (4) can be locked in a deployment position, with the module (4) still remaining pivotally elastic and/or in a spring-like fashion.

5. A hearing protection and/or loudspeaker element according to claim 1, wherein the holding element (8) and thus also the module (4) and thus also the entire hearing protection and/or loudspeaker element (1) is held on the carrier part (2) perpendicular to a deployment direction thereof and adjustable in the vertical and/or horizontal direction.

6. A hearing protection and/or loudspeaker element according to claim 1, wherein the carrier part (2) is mounted to a helmet or is a part thereof.

7. A hearing protection and/or loudspeaker element according to claim 6, wherein the adjustment device for the module (4) is operable from an outside of the helmet (5).

8. A hearing protection and/or loudspeaker element according to claim 1, wherein two of the carrier parts (2) with respective ones of the modules (4) are mounted to end sections of an arched part that can be worn.

9. A hearing protection and/or loudspeaker element according to claim 6, wherein the helmet (5) comprises a vehicular protective helmet.

* * * * *